United States Patent [19]

Schmidt et al.

[11] Patent Number: 4,770,781

[45] Date of Patent: Sep. 13, 1988

[54] PURIFICATION OF HUMAN INTERLEUKIN-1 SPECIES

[75] Inventors: Jack A. Schmidt, Mahwah; Patricia M. Cameron, Rahway; Guadalupe A. Limjuco, Edison, all of N.J.

[73] Assignee: Merck & Co., Inc., Rahway, N.J.

[21] Appl. No.: 80,182

[22] Filed: Jul. 29, 1987

Related U.S. Application Data

[63] Continuation of Ser. No. 835,676, Mar. 3, 1986, abandoned, which is a continuation-in-part of Ser. No. 769,231, Aug. 26, 1985, abandoned.

[51] Int. Cl.$^4$ .............................................. B01D 15/08
[52] U.S. Cl. .................................. 210/635; 210/656; 530/351; 530/413; 530/417
[58] Field of Search .................. 530/413, 417, 351; 435/68, 70, 71, 83; 210/635, 656–659, 198.2, 198.3

[56] References Cited

U.S. PATENT DOCUMENTS

| | | | |
|---|---|---|---|
| 3,960,720 | 6/1976 | Porath | 210/635 |
| 4,006,059 | 2/1977 | Butler | 530/415 |
| 4,289,690 | 9/1981 | Pestka | 530/351 |
| 4,359,389 | 11/1982 | Heine | 210/656 |
| 4,377,482 | 3/1983 | Rivier | 210/635 |
| 4,416,783 | 11/1983 | Noguchi | 210/365 |
| 4,443,307 | 4/1984 | Moore | 210/737 |
| 4,485,017 | 11/1984 | Tan | 210/635 |
| 4,490,289 | 12/1984 | Stern | 530/351 |
| 4,508,833 | 4/1985 | Sonneborn | 530/351 |
| 4,528,134 | 7/1985 | Stentz | 210/659 |

OTHER PUBLICATIONS

Snyder, Introduction to Modern Liquid Chromatography, John Wiley & Sons, Inc., New York, 1979, pp. 662–686.
Mike's Handbook of Chromatographic and Allied Methods Ellis Horwood Limited, Chichester, 1979, pp. 557–561.
Chang "High Speed Ion Exchange Chromatography of Proteins" Analytical Chemistry, vol. 48, No. 13, 1976, pp. 1839–1845.
Gillis et al., J. Immunol., (1978), 120:2027–2032.
Hewick et al., J. Biol. Chem., (1981), 256:7990–7997.
Kronheim et al., J. Exp. Med., (1985), 161:490–502.
Lachman et al., J. Supramol. Struc., (1980), 13:457–466.
Mizel et al., J. Immunol., (1978), 120:1497–1503.
Schmidt, J. Exp. Med., (1984), 160:772–787.
Schmidt et al., J. Immunol., (1982), 128:2177–2182.
Kock and Luger, J. Chromat., (1984), 296:293–300.
Krakauer, Prep. Biochem., (1984/85), 14:449–470.
Dewhirst et al., J. Immunol., (1985), 135:2562–2568.

*Primary Examiner*—Ernest G. Therkorn
*Attorney, Agent, or Firm*—Jack L. Tribble; Hesna J. Pfeiffer; Donald J. Perrella

[57] ABSTRACT

Human interleukin-1 (IL-1) charged species (pI 6.8, 6.0, 5.4 and 5.2) are separated and purified by a rapid and efficient two or three stage chromatographic process. Interleukin-1 species present in concentrated culture fluid from stimulated human mononuclear cells are separated and partially purified by anion exchange high performance liquid chromatography. The pI 5.4 and 5.2 species in addition are partially purified by HPLC gel filtration chromatography. Each of the individual IL-1 species are then finally purified by reverse phase high performance liquid chromatography. This process results in homogenously pure pI 6.8, pI 5.4 and pI 5.2 species while the pI 6.0 species is isolated in a substantially pure form.

12 Claims, No Drawings

PURIFICATION OF HUMAN INTERLEUKIN-1 SPECIES

RELATED U.S. APPLICATION DATA

This is a continuation of application Ser. No. 835,676, filed Mar. 3, 1986, which is a continuation-in-part of U.S. Ser. No. 769,231, filed Aug. 26, 1985, both now abandoned.

BACKGROUND OF THE INVENTION

The present invention relates to a rapid and efficient method of separation and purification of the four species of human interleukin-1 (IL-1).

A growing body of in vitro and in vivo data strongly suggests that interleukin-1 (IL-1) plays a central hormonal role in acute and chronic inflammation. For example, IL-1 has been shown to stimulate fever, the synthesis of acute phase reactants by the liver, and the proliferation of connective tissue cells involved in fibrosis. Moreover, IL-1 can stimulate in vitro the production of prostaglandins and collagenase by chondrocytes and rheumatoid synovial cells and therefore may be responsible for the destruction of articular cartilage in rheumatoid arthritis. No other inflammatory mediator is known to have this property. Interleukin-1 has also been implicated in beneficial tissue responses, such as enhanced anti-tumor activity resulting from the stimulation of natural killer cells. This diversity of biological activities suggests that the identified human IL-1 species may have different effector cell functions. To date at least four biologically active species of human IL-1 have been identified by isoelectrofocusing with isoelectric points (pI) of about 6.8 to about 7.2 (herein denoted pI 6.8), about 5.8 to about 6.2 (herein denoted pI 6.0), about 5.3 to about 5.5 (herein denoted pI 5.4) and about 5.0 to about 5.3 (herein denoted pI 5.2) (Lachman et al., J. Supramol. Struct., (1980) 13: 457–466, Schmidt et al., J. Immunol., (1982) 128: 2177–2182). The ability to unequivocally correlate biological activity with IL-1 species levels has been forestalled by the lack of highly purified human IL-1 species. Methods of purification of human IL-1 have been described in the literature but most have not purified the individual species of IL-1. Lachman et al., J. Supramol. Struct., (1980) 13: 457–466, describe a gel filtration, isoelectric focusing and polyacrylamide gel electrophoresis separation technique that results in a partially pure IL-1 preparation. Kronheim et al., J. Exp. Med., (1985) 161: 490–502, describe a multistep purification procedure that results in a preparation containing at least three of the four species of human IL-1. Schmidt, J. Exp. Med., (1984) 160: 772–787, describes a method for the purification of human IL-1 species pI 6.8 using ion exchange high pressure liquid chromatography (HPLC) in the isocratic mode followed by size exclusion HPLC. This procedure resulted in a pure preparation of the pI 6.8 species but there are several major disadvantages to this technique. First, the isocratic separations were extremely time consuming and had limited product capacity. Second, it was necessary to repeat the isocratic anion exchange HPLC in order to remove contaminants which were not entirely removed during the first step. Third, the size exclusion HPLC resulted in dilution of the sample as well as suspension of the sample in non-lyophilizable salts and thus made it difficult to use the purified material for subsequent procedures.

OBJECTS OF THE INVENTION

It is, accordingly, an object of the present invention to provide a procedure for the purification of the various species of IL-1. Another object is to provide a method which will allow the separation of all the biologically active species of IL-1 in higher purity and greater yield. A further object is to provide a method which permits recovery of the purified interleukin-1 species in a shorter period of time than heretofore possible. These and other objects of the present invention will be apparent from the following description.

SUMMARY OF THE INVENTION

Interleukin-1 species present in concentrated culture fluid from stimulated human mononuclear cells are separated by anion exchange high performance liquid chromatography. The pI 5.4 and pI 5.2 species are pre-purified by HPLC gel filtration chromatography. The individual IL-1 species are further purified by reverse phase high performance liquid chromatography. This unique methodology provides IL-1 species in greater purity, higher yields and in a shorter time than heretofore possible.

DETAILED DESCRIPTION

The present invention relates to a simple two or three-stage method for the separation and purification of human interleukin-1 species. The dominant IL-1 species, pI 6.8 is collected in a homogenously pure form as are the individual acidic species of IL-1, pI 5.4 and pI 5.2 while the pI 6.0 species is collected in substantially pure form. The term "homogenously", as used herein, refers to a single polypeptide that has been separated from functionally similar but chemically different polypeptides and said peptide has been purified and is shown to be free of other peptides by various physiochemical tests. These tests include, but are not limited to, analytical isoelectrofocusing, SDS polyacrylamide gel electrophoresis, amino terminal sequencing and ultraviolet light absorbance profiles of sample eluates. The term "substantially", as used herein, refers to a single polypeptide that has been characterized by at least one of the tests described above but has not been subjected to all of the tests.

This invention provides a rapid and efficient method of purifying interleukin-1 species derived from human mononuclear cells. Peripheral blood mononuclear cells are collected by leukophoresis and purified by discontinuous density gradient centrifugation. The mononuclear cells are cultured under serum free conditions for at least four days in the presence of stimulants, e.g., phytohemagglutinin, lipopolysaccharide, silica and killed bacteria with phytohemagglutinin and lipopolysaccharide being preferred for the stimulation of IL-1 production. The culture fluid containing crude IL-1 is concentrated by ultrafiltration, vacuum dialysis, isoelectrofocusing and lyophilization, with ultrafiltration being preferred and prepared for separation by dialysis against the buffer used for separation, e.g., 20 mM TRIS acetate, pH about 8.3 to about 8.5. The sample is placed on a DEAE HPLC column equilibrated with the same buffer and eluted by an acceptable eluant such as a linear descending pH gradient with 20 mM TRIS acetate, pH about 6.7 to about 6.9. Elution samples are collected at times ranging from about 25 minutes to about 150 minutes. Interleukin-1, species pI 6.8, typically elutes as a single peak between 125 and 144 minutes. The descending pH gradient used on the anion exchange HPLC column is very selective as compared to standard salt gradient elution techniques used previously for the separation of IL-1 species pI 6.8. A single passage of crude supernatant gives IL-1, species pI 6.8, preparations that are approximately 70-80% pure.

Separation of the acidic species of human IL-1 including pI 6.0, 5.4 and 5.2 may be accomplished by a second elution of the DEAE HPLC column following collection of IL-1 species pI 6.8 or by elution of crude extract without the prior elution of the pI 6.8 species. Elution of the acidic species was achieved by the use of an acceptable eluant such as, a linear gradient of a salt, e.g., sodium acetate, in TRIS buffer, pH about 6.7 to about 6.9. Elution samples are collected at times ranging from about 10 minutes to about 100 minutes. The separated acidic species of human IL-1 eluted as three distinct peaks between about 37 and about 75 minutes after initiation of the gradient. The pI 5.4 and pI 5.2 species are partially purified by gel filtration chromatography, preferably HPLC gel filtration (size exclusion) chromatography. The filtration-exclusion matrix consists of silica with the surface silanols derivatized with hydrophilic organiosilanes such as glycerylpropyltrimethoxysilane or N-acetylaminopropylsilane, with glycerylpropyltrimethyloxysilane prefered.

The derivatized silica matrix allows the separation of molecules with molecular weights of from about 5,000 to about 150,000. The IL-1 species pI 5.4 and pI 5.2 are chromatographed employing an acceptable buffer such as, phosphate buffer, preferably sodium phosphate with a pH of about 6.8. The biological activity of all IL-1 fractions is determined using the mouse thymocyte stimulation assay.

The active fractions of each IL-1 species from the preliminary separations and partial purification are pooled, concentrated and loaded on a reverse phase HPLC column, consisting of an alkyl silane substrate wherein the alkyl group has from 3 to 8 carbon atoms, preferably 4 carbons. The column is equilibrated with an organic acid, e.g. trifluoroacetic acid (TFA), about 0.1% in water and the individual IL-1 species are loaded on separate columns for purification. The IL-1 species are eluted by a gradient of from 0-50% of an acid in an organic solvent, e.g., acetonitrile also containing an organic acid, e.g., about 0.1% TFA. Elution samples are collected from about 12 to about 18 minutes. The purified IL-1 species pI 6.8 typically eluted as a sharp, dominant peak at between about 11.6 and about 11.9 minutes. The acidic species, that is those with a pI of 5.2, a pI of 5.4 and a pI of 6.0 elute at between about 13 and about 23 minutes. Biological activity of the purified fraction is determined by the mouse thymocyte stimulation assay. The use of the reverse phase HPLC as the final step is advantageous because the purified proteins are isolated in volatile, high purity buffers suitable for sequence analysis, amino acid analysis, and other types of biochemical and biological analysis.

The human IL-1 species which is eluted from the DEAE HPLC column with a pH gradient, and is further purified by reverse phase HPLC, has a pI of about 6.8 as determined by analytical isoelectrofocusing. Further chemical analysis using SDS polyacrylamide gel electrophoresis and amino terminal amino acid sequencing demonstrates that the purified IL-1 species pI 6.8 consists of a single band with a molecular weight of about 15,000 to about 18,000 and contains a single amino terminus, respectively. Biological activity of the purified pI 6.8 species as determined by the murine thymocyte assay shows a specific activity of $1.9 \times 10^7$ half-maximal units per mg of protein. This represents nearly a 800-fold purification with a recovery of biological activity between 15 and 20 percent. Approximately 20 $\mu$g of material can be produced per 5 liters of culture supernatant. Analysis of the purified acidic species of human IL-1 reveals three biologically active fractions as determined by the murine thymocyte assay. As with the pI 6.8 species, the final purification of the acidic species, pI 5.4 and pI 5.2, using reverse phase HPLC results in a single absorbance peak when rechromatographed by reverse phase HPLC. Following analysis by SDS PAGE and silver staining in parallel with IL-1 pI 6.8 it is seen that each species formed a single band in the 17-18 kd range. Analytical isoelectric focusing shows that the two species purified by the described protocol have pI's of 5.4 and 5.2 respectively. The reverse phase HPLC profile for IL-1 species pI 6.0, reveals a single, sharp peak suggesting that the material is highly purified given the high-resolving power of the technique. In the murine thymocyte proliferation assay species pI 6.8, pI 5.4 and pI 5.2 gave half maximal stimulation at a concentration of approximately 150 pg/ml or $1 \times 10^{-11}$M.

The resulting purified human IL-1 species are essential for the physiochemical characterization of each species and for comparisons between species. The purified species will ensure the correct amino acid sequence of the species and will allow the synthesis of nucleic acid probes for the identification of individual IL-1 cDNA. The availability of purified human IL-1 species is fundamental to the correlation of chemical structure with biological activity. Indeed, it will now be possible to determine which species of IL-1 are responsible for the beneficial activities, such as the activation of natural killer cells in anti-tumor responses and the stimulation of fibroblasts in wound healing and which species induce the deleterious responses, such as the release of mediators involved in chronic inflammation. Purified human IL-1 species will allow the therapeutic assessment of specific IL-1 antagonists. The search for such antagonists has been impeded because purified human IL-1 species have not been available. The purified human IL-1 species can also be used to produce polyclonal and monoclonal antibodies which can be used in assays to quantitate IL-1 species in fluids and tissues. This purification procedure will be ideal for the purification of IL-1 species derived from human macrophage tumor cell lines and recombinant derived IL-1 isolated from in vitro translational systems.

A particular advantage of this purification technique is the ease with which the elution buffer containing TFA in acetonitrile can be removed from the purified IL-1 species. For further chemical analysis the buffer can be removed by lyophilization. For biological evaluation of the IL-1 species the eluate liquid from the purification step can be diluted with a physiologically acceptable medium or the lyophilized IL-1 species can be reconstituted in said medium. Such physiologically acceptable media include, but are not limited to, physiological saline, phosphate buffered saline, Ringer's solution, Hank's solution and the like.

The following examples illustrate the present invention without, however, limiting the same thereto.

EXAMPLE 1

Preparation of Crude Human Interleukin-1

Human peripheral blood monocytes were collected by leukophoresis using an IBM 2997 blood cell separator and purified by Ficoll Paque (Pharmacia) discontinuous density gradient centrifugation at 250 ×g. The cells, $5 \times 10^6$/ml, were cultured in upright flasks, 75 cm$^2$, containing 100 ml of serum free medium, RPMI-1640, supplemented with 20 mM Hepes, 4 mM glutamine, 100 μ/ml penicillin and 100 μg/ml streptomycin and containing both phytohemagglutinin (5 μg/ml) and lipopolysaccharide (1 μg/ml) for 4 days at 37° C. in a humidified atmosphere of 5% $CO_2$-95% air. The crude culture supernatant liquids were concentrated approximately 20-fold by ultrafiltration using a Pellicon cassette equipped with 0.5 ft$^2$ of a PT membrane (Millipore) having a molecular weight exclusion limit of 10,000. A further concentration of nearly 50-fold was achieved by ultrafiltration using an Amicon YM-10 membrane.

EXAMPLE 2

Separation of Crude IL-1 by Anion Exchange High Performance Liquid Chromatography The crude concentrated supernatant liquid from Example 1 was dialyzed against buffer A (20 mM TRIS acetate, pH 8.3), and loaded on an HPLC DEAE column [Bio-Gel TSK-DEAE-5-PW (21.5×150 mm), Bio-Rad] at a flow rate of 4 ml per minute that was equilibrated in the same buffer. Forty minutes after injection a linear descending pH gradient from 0-50% B (buffer B: 20 mM TRIS acetate, pH 6.8) was initiated at a rate of 0.5% B/minute. The absorbance of the column effluent was monitored at 210 nm and fractions were collected every 30 seconds. The IL-1, species pI 6.8, bioactivity typically eluted as a sharp peak between 126 and 142 minutes from the time of eluent application. Separation of the acidic species of IL-1 was accomplished by subsequent elution from the same column with a linear gradient of 1 M sodium acetate (0-0.3 M) in 20 mM TRIS buffer, pH 6.8, at a rate of 3 mM per minute for 100 minutes. Absorbance of the column effluent was monitored at 280 nm and fractions were collected every 30 seconds. The acidic species of human IL-1 typically eluted as three sharp distinct peaks between 37 and 80 minutes from the time of eluent application. The biological activity of the IL-1 species was determined by a murine thymocyte proliferation assay [Mizel et al., (1978), J. Immunol. 120: 1497-1503]. Samples were assayed in parallel with aliquots of a partially purified preparation of IL-1 which consistently gave 550 half-maximal units per ml. Units of IL-1 activity were calculated by established criteria [Gillis et al., (1978), J. Immunol. 120: 2027-2032].

EXAMPLE 3

Partial Purification of Interleukin-1 Species pI 5.4 and pI 5.2 by High Performance Liquid Chromatography Gel Filtration Chromatography The active fractions of each IL-1 species, pI 5.4 and pI 5.2 from Example 2 were pooled and combined with 10 μg/ml aprotinin, 1 μM PMSF and 0.025 M EDTA. Each pool was concentrated to a volume of 2 ml by ultrafiltration using YM-10 membranes (Amicon) and fractionated by HPLC gel filtration chromatography. The separation was performed on a preparative TKS-2000 SW column (21.5×600 mm; BioRad), consisting of trimethylsilane coated silica beads with exclusion limits of between about 5,000 and about 150,000 molecular weight, in 100 mM sodium phosphate buffer, pH 6.8, containing 20% ethylene glycol (v/v) at a rate of 3 ml/min. The IL-1 activity eluted between 122 and 132 mls.

EXAMPLE 4

Purification of Interleukin-1 Species by Reverse Phase High Performance Liquid Chromatography The active fractions of each IL-1 species from Example 2 and Example 3 were pooled and concentrated by ultrafiltration using a YM-10 membrane (Amicon) to a volume of 1 ml, and loaded on a Vydac C4 reverse phase HPLC column (0.4×5 cm; Separations Group) equilibrated in 0.1% TFA/$H_2O$. The flow rate was 1 ml/minute. In the case of IL-1 pI 6.8, the column was eluted with a gradient from 0-50% B (buffer B: 0.1% TFA/acetonitrile) at a rate of 10% B per minute for 3 minutes and 2% B per minute for 10 minutes. In the case of IL-1 pI 5.4 and pI 5.2 the column was eluted with a gradient of 0-40% B at a rate of 9% per minute for 4 minutes and then 0.25% B for 16 minutes at a reduced flow rate of 0.5 ml per minute. The absorbance of the column effluent was monitored at 210 nm for all species. Fractions were collected every 30 seconds by a Pharmacia Frac-100 fraction collector equipped with a programmable peak collection device. The IL-1, species pI 6.8, bioactivity eluted as a single sharp peak at 11.8 minutes. The acidic species, that is those with a pI of 5.2 and a pI 5.4 elute at 20.0 minutes and 20.5 minutes respectively. Biological activity of the fractions was evaluated by the murine thymocyte stimulation assay.

The purity of human IL-1 species pI 6.8 was demonstrated by SDS polyacrylamide gel electrophoresis in 15% homogeneous gels under reducing conditions. The protein formed a single homogeneous band having a molecular weight of 18,000. When analyzed by analytical isoelectric focusing there was a single band with a pI of 6.8. The purity of human IL-1 species pI 6.8 was also demonstrated by amino terminal sequence analysis according to the method of Hewick et al., J. Biol. Chem. 256:7990-7997 (1981) and employing an automated gas-phase sequencer (Model 470A, Applied Biosystems), which revealed a single amino terminus. The final purification of the acidic species, pI 5.4 and pI 5.2, using reverse phase HPLC results in a single absorbance peak when each species was rechromatographed by reverse phase HPLC. Homogenity of the pI 5.4 and pI 5.2 species is determined by SDS PAGE and silver staining. Each species migrates as a single hand with a molecular weight between 17 and 18 kd. The isoelectric points of the purified species pI 5.4 and pI 5.2 were confirmed by analytical isoelectric focusing. The specific bilogical activity of the pI 5.4 and pI 5.2 species was the same as the pI 6.8 species in the murine thymocyte assay.

EXAMPLE 5

Protein Concentration of Human Interleukin-1 Species pI 6.8, pI 5.4 and pI 5.2

Amino acid analysis was used to determine the concentration of purified IL-1, pI 6.8, protein. Duplicate samples (25-30 pmoles) were taken to dryness and hydrolyzed under nitrogen with gaseous HCl for 20 hours at 105° C. The hydrolysate was derivatized with phenylisothiocyanate (PITC) to form phenylthiocarbamyl amino acid derivatives which were separated by reverse phase HPLC using a C18 microbondapak (Waters Associates) reverse phase column. The peaks were identified and quantitated by chromatography and integration of standard amino acid mixtures (Pierce) which were derivatized with PITC in identical fashion. The standard error of the mean obtained for each of the 17 assayable amino acids was always less than 10% of the mean and usually less than 5% of the mean. Values obtained for tyrosine, isoleucine, and leucine were particularly reproducible and were used for mass determinations using values of 4, 5 and 15 moles, respectively, per mole of IL-1. Amino acid analysis gives a more accurate measure of protein concentration than procedures heretofore used. This in turn allows a more exacting calculation of the IL-1 specific biological activity as determined by the murine thymocyte proliferation assay.

A summary of the purification protocol of human IL-1, species pI 6.8, is presented in Table 1. This procedure provides approximately a 800-fold purification of human IL-1, pI 6.8, with a minimum of 15% recovery of starting biological activity. The specific activity of the homogenously pure IL-1 is $1.8 \times 10^7$ half-maximal units per mg of protein.

TABLE 1

Purification of Normal Human Interleukin-1

| Step | Total Activity (Units) | Total Protein (mg) | Specific Activity (units/mg) | Times Purified | Yield % |
|---|---|---|---|---|---|
| 1. Crude | $2.6 \times 10^6$ | 105 | $2.5 \times 10^4$ | — | 100 |
| 2. Crude Conc. | $2.9 \times 10^6$ | 95 | $3.1 \times 10^4$ | 1.2 | 111 |
| 3. Anion Exchange, HPLC | $3.0 \times 10^5$ | 0.036 | $8.3 \times 10^6$ | 332 | 12 |
| 4. Reverse Phase HPLC | $3.9 \times 10^5$ | 0.021 | $1.8 \times 10^7$ | 760 | 15 |

Integration of the absorbance profile obtained at 210 nm during reverse phase HPLC was used to determine the concentration of purified IL-1, pI 5.2 and purified IL-1, pI 5.4 protein. The integration was performed by a Nelson Analytical Data Acquisition System, Model 4416, run on a Hewlett Packard 9816 computer. Known amounts of pure ribonuclease were used to calibrate the integration function of the Data Acquisition System. The purification protocol for pI 5.4 and pI 5.2 results in approximately a 4000 fold purification with 6% recovery of initial biological activity.

What is claimed is:

1. A method of chromatographically separating biologically active individual human interleukin-1 species, pI 6.8, pI 6.0, pI 5.4 and pI 5.2 from a mixture containing human interleukin-1 species comprising high performance liquid chromatography with an anion exchange functional group and subsequently in either order:
   recovering interleukin-1 species, pI 6.8 by eluting with a first eluant and
   recovering as separate active fractions pI 6.0, pI 5.4, and pI 5.2 with a second different eluant.

2. A method according to claim 1 wherein the anion exchanger functional group is diethylaminoethyl.

3. A method according to claim 1 wherein human interleukin-1 species pI 6.8 is eluted with a pH gradient.

4. A method according to claim 3 wherein the eluant is a descending pH gradient.

5. A method according to claim 1 wherein human interleukin-1 species pI 6.0, pI 5.4 and pI 5.2 are separated by elution with a salt gradient.

6. A method according to claim 5 wherein the salt is sodium acetate.

7. A method of partially purifying the biologically active individual human interleukin-1 species, pI 5.4 and pI 5.2 separated by the method of claim 1 comprising size exclusion gel filtration high performance liquid chromatography with a derivatized silica matrix and an acceptable eluant.

8. A method according to claim 7 wherein the derivatized matrix is trimethylsilane.

9. A method according to claim 8 wherein the matrix allows the separation of molecules with a size of between 5,000 to 150,000 kd.

10. A method according to claim 7 wherein the eluant consists of a buffer solution and an alcohol.

11. A method according to claim 10 wherein the alcohol is 1,2-ethanediol.

12. A method of chromatographically purifying the biologically active individual human interleukin-1 species, pI 6.8 and pI 6.0 separated by the method of claim 1 or species pI 5.4 and pI 5.2 partially purified by the method of claim 7 further comprising reverse phase high performance liquid chromatography using an alkyl silane substrate containing 4 carbon atoms and an eluant containing trifluoroacetic acid and acetonitrile.

* * * * *